(12) United States Patent
Inokawa et al.

(10) Patent No.: US 10,124,320 B1
(45) Date of Patent: Nov. 13, 2018

(54) VANADIUM OXIDE CATALYST SUPPORTED ON $CEO_2$—$ZRO_2$ FOR DIMETHYL ETHER PRODUCTION VIA OXIDATIVE DEHYDRATION OF METHANOL

(71) Applicant: King Abdulaziz University, Jeddah (SA)

(72) Inventors: Hitoshi Inokawa, Jeddah (SA); Sharif F. Zaman, Jeddah (SA); Muhammad A. Daous, Jeddah (SA); Abdulrahim Al-Zahrani, Jeddah (SA); Lachezar Petrov, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/813,215

(22) Filed: Nov. 15, 2017

(51) Int. Cl.
| | |
|---|---|
| *B01J 21/06* | (2006.01) |
| *B01J 23/10* | (2006.01) |
| *B01J 23/22* | (2006.01) |
| *B01J 35/00* | (2006.01) |
| *B01J 37/00* | (2006.01) |

(Continued)

(52) U.S. Cl.
CPC ............ *B01J 23/22* (2013.01); *B01J 21/066* (2013.01); *B01J 23/10* (2013.01); *B01J 35/002* (2013.01); *B01J 37/0036* (2013.01); *B01J 37/0072* (2013.01); *C07C 41/09* (2013.01); *C07C 43/043* (2013.01)

(58) Field of Classification Search
CPC . B01J 23/10; B01J 23/22; B01J 35/002; B01J 21/066; B01J 37/0036; B01J 37/0072; C07C 41/09; C07C 43/043
See application file for complete search history.

(56) References Cited

U.S. PATENT DOCUMENTS

| | | | | |
|---|---|---|---|---|
| 5,958,827 A | * | 9/1999 | Suda ............... | B01D 53/945 502/300 |
| 6,458,741 B1 | * | 10/2002 | Roark ............... | A62D 3/38 423/245.3 |

(Continued)

FOREIGN PATENT DOCUMENTS

| | | |
|---|---|---|
| CN | 104117363 | 10/2014 |
| CN | 104148087 | 6/2016 |

OTHER PUBLICATIONS

Benjaram M. Reddy et al., "Structural Characterization of CeO2—ZrO2/TiO2 and V2O5/CeO2—ZrO2/TiO2 Mixed Oxide Catalysts by XRD, Raman Spectroscopy, HREM, and Other Techniques," Journal of Physical Chemistry, 2005, vol. 109, No. 5, pp. 1781-1787. http://pubs.acs.org/doi/abs/10.1021/jp045723%2B?journalCode=jpcbfk.

(Continued)

*Primary Examiner* — Cam N. Nguyen
(74) *Attorney, Agent, or Firm* — Oblon, McClelland, Maier & Neustadt, L.L.P.

(57) ABSTRACT

A catalyst of vanadium oxide supported on cerium oxide and zirconium oxide is specified. The catalyst comprises 0.1-10 wt % vanadium oxide relative to the total catalyst weight, and the catalyst is in the form of microparticles. A method using a wetness impregnation technique to produce the catalyst is described. The use of the catalyst in the oxidative dehydration of methanol to produce dimethyl ether is specified, along with the catalyst's stability for reaction periods of 50 or more hours.

13 Claims, 14 Drawing Sheets

(51) Int. Cl.
*C07C 41/09* (2006.01)
*C07C 43/04* (2006.01)

(56) References Cited

U.S. PATENT DOCUMENTS

| | | | | |
|---|---|---|---|---|
| 6,528,451 | B2 * | 3/2003 | Brezny | B01D 53/945 423/263 |
| 7,166,263 | B2 * | 1/2007 | Vanderspurt | B01J 23/002 423/263 |
| 7,211,236 | B2 | 5/2007 | Stark et al. | |
| 7,384,888 | B2 * | 6/2008 | Kuno | B01D 53/945 502/302 |
| 7,871,956 | B2 * | 1/2011 | Wakita | B01D 53/945 423/593.1 |
| 7,919,429 | B2 * | 4/2011 | Okamoto | B01D 53/945 502/302 |
| RE44,802 | E * | 3/2014 | Kuno | 502/302 |
| 9,962,684 | B2 * | 5/2018 | Hayashida | B01J 23/10 |

OTHER PUBLICATIONS

Benjaram M Reddy et al., "Raman and X-ray photoelectron spectroscopy study of CeO2—ZrO2 and V2O5/CeOO2—ZrO2 catalysts," Langmuir, Apr. 3, 2003, vol. 19, No. 7, pp. 3025-3030, https://www.researchgate.net/publication/244405374.

\* cited by examiner

*Aluminum from sample holder

VANADIUM OXIDE CATALYST SUPPORTED ON $CEO_2$—$ZRO_2$ FOR DIMETHYL ETHER PRODUCTION VIA OXIDATIVE DEHYDRATION OF METHANOL

BACKGROUND OF THE INVENTION

Technical Field

The present invention relates to a catalyst of vanadium oxide supported on cerium oxide and zirconium oxide, methods of synthesis, and methods of use as a catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dimethyl ether (DME) has attracted great attention as a possible substitute of diesel fuel, because of its physical and chemical properties. The DME molecule does not contain a C—C bond. For this reason only small amounts of soot are formed during the combustion process. DME is colorless and not toxic, and can be mixed with liquefied petroleum gas (LPG). DME itself can be liquefied at room temperature (20-30° C.) at a pressure of 7 bars, and can be stored and transported in a liquid form without undue hazards.

DME can be used not only as a diesel fuel but also as a starting chemical in the production of many valuable products. DME can be transformed into valuable organic chemicals like olefins, aromatics, methyl acetate, formaldehyde, and ethanol. See Song, W. et al., *Journal of the American Chemical Society*, 124 (2002) 3844-3845; Cheung, P. et al., *Angewandte Chemie International Edition*, 45 (2006) 1617-1620; Liu, H. et al., *Journal of Catalysis*, 217 (2003) 222-232; and Li, X. el al., *ChemSusChem*, 3 (2010) 1192-1199, each incorporated herein by reference in its entirety. Thus, DME has a huge and diverse commercial potential.

The annual global consumption of DME in 2014 was 3,740,460 tons. The expected consumption growth rate for the period 2015-2020 is 15.67%. See "Dimethyl Ether Market by Raw Materials (Coal, Methanol, Natural gas and Bio-based feedstock), by Applications (Aerosol Propellant, LPG Blending, Transportation fuel and Others), and by Region—Trends & forecasts to 2020," *MarketstandMarkets*, 2015, incorporated herein by reference in its entirely.

DME is industrially produced mainly by the dehydration of methanol. Generally, mild acidic catalysts are used to catalyze this process. See Sun, J. et al., *ACS Catalysis*, 4 (2014) 3346-3356, incorporated herein by reference in its entirety. Alumina ($\gamma$-$Al_2O_3$) based catalysts have the widest industrial use because of their low cost, high DME selectivity, and great thermal and mechanical stability. See Sun, J. et al., *ACS Catalysis*, 4 (2014) 3346-3356; Akarmazyan, S. S. et al., *Applied Catalysis B: Environmental*, 145 (2014) 136-148; Liu, D. et al., *Fuel*, 90 (2011) 1738-1742, each incorporated herein by reference in its entirety. A summary of the reported performance of $\gamma$-$Al_2O_3$ and other catalysts is reported in Table 1.

TABLE I

Catalytic activity and selectivity performance of existing DME catalysts.

| Catalyst | Temp. (° C.) | Space Velocity of $CH_3OH$ ($h^{-1}$ $g_{cat}^{-1}$) | Degree of Conversion (%) | Selectivity of DME (%) | Reference* |
|---|---|---|---|---|---|
| $\gamma$-$Al_2O_3$ | 150-400 | 2500 | 90 | 100 | Akarmazyan, et al. |
| $\gamma$-$Al_2O_3$ modified with $Nb_2O_5$ | 240-340 | 1 | 87 | No info | Liu, et al. |
| $\gamma$-$Al_2O_3$ modified with $SiO_2$ | 300 | 15600 | 86.4 | 100 | Yaripour, et al. |
| H—Y, and Fe—, Co—, Ni—, Cr—, Zi— ion exchanged Y zeolite | 245 | 6000 | 86 | No info. | Fei, et al. |
| H—Y zeolite | 245 | 6000 | 87.5 | 92.1 | Jin, et al. |
| $TiO_2$ | 300 | 6.9 $mmol_{CH3OH}$ $h^{-1}$ $g_{cat}^{-1}$ | 4 | 84 | Ladera, et al. |
| $WO_x$ modified $TiO_2$ | 300 | 6.9 $mmol_{CH3OH}$ $h^{-1}$ $g_{cat}^{-1}$ | 15 | 82 | Ladera, et al. |

*See Akarmazyan, S.S. et al., *Applied Catalysis B: Environmental*, 145 (2014) 136-148; Liu, D. et al., *Fuel*, 90 (2011) 1738-1742; Yaripour, F. et al., *Catalysis Communications*, 6 (2005) 147-152; Fei, J. et al., *Applied Catalysis A: General*, 304 (2006) 49-54; Jin, D. et al., *Fuel*, 86 (2007) 2707-2713; and Ladera, R. et al., *Fuel*, 113 (2013)1-9, each incorporated herein by reference in its entirety.

Zeolites (such as HZSM-5, HY, HZSM-22, H-SAPO, and many others) have strong acidic sites and therefore have been widely investigated as potential industrial catalysts for dehydration of methanol. See Fei, J. et al., *Applied Catalysis A: General*, 304 (2006) 49-54; Jin, D. et al., *Fuel*, 86 (2007) 2707-2713; Moses, P. G. et al., *ACS Catalysis*, 3 (2013) 735-745; and Yang, Q. et al., *Energy & Fuels*, 26 (2012) 4475-4480, each incorporated herein by reference in its entirety. Unfortunately, a formation of considerable amounts of different byproducts such as hydrocarbons as well as coke takes place parallel to the main reaction, which results in a fast catalyst deactivation.

In view of the foregoing, one objective of the present invention is to provide a $CeO_2$ and $ZrO_2$ supported vanadium oxide catalyst, a method of making the catalyst, and a method of using the catalyst in the oxidative dehydration of methanol to produce dimethyl ether.

BRIEF SUMMARY OF THE INVENTION

According to a first aspect, the present disclosure relates to a $CeO_2$ and $ZrO_2$ supported vanadium oxide catalyst, comprising: 0.1-10 wt % vanadium; 65-80 wt % $CeO_2$; and 20-32 wt % $ZrO_2$. This catalyst is in the form of microparticles with diameters of 50-200 μm.

In one embodiment, the catalyst has a surface area of 80-150 $m^2/g$.

In one embodiment, the catalyst has a Ce to Zr molar ratio of 1.4:1-3.5:1.

In one embodiment, the vanadium oxide is $V_2O_5$.

According to a second aspect, the present disclosure relates to a method for producing the $CeO_2$ and $ZrO_2$ supported vanadium oxide catalyst of the first aspect. This method involves mixing $CeO_2$, $ZrO_2$, a vanadium compound, and water to form a solution; drying the solution to produce a dried catalyst precursor; heating the dried catalyst precursor at 450-700° C. for 2-8 hours to produce a calcined catalyst sample; and pelletizing and grinding the calcined catalyst sample to produce the $CeO_2$ and $ZrO_2$ supported vanadium oxide catalyst.

In one embodiment of the method, the solution has a vanadium concentration of 0.05-1.0 M.

In one embodiment of the method, the vanadium compound is one selected from the group consisting of ammonium metavanadate, potassium metavanadate, sodium metavanadate, bismuth vanadate, vanadium oxytrichloride, vanadium pentafluoride, and vanadium oxide.

In a further embodiment, the vanadium compound is ammonium metavanadate.

According to a third aspect, the present disclosure relates to a method of dehydrating methanol into dimethyl ether. This method involves feeding a gas stream comprising $O_2$ and methanol to a fixed bed flow reactor comprising the $CeO_2$ and $ZrO_2$ supported vanadium oxide catalyst of the first aspect at a temperature of 200-300° C. to produce dimethyl ether and at least one side product selected from the group consisting of hydrogen gas, carbon monoxide, carbon dioxide, water, and formaldehyde.

In one embodiment, the gas stream has an $O_2$ to methanol molar ratio of 0.2:1-0.6:1.

In one embodiment, the gas stream is fed to the fixed bed flow reactor at a gas hourly space velocity of 25,000-35,000 $h^{-1}$.

In one embodiment, a selectivity percentage for dimethyl ether from the conversion of methanol is at least 90%.

In one embodiment, a percentage yield of dimethyl ether, relative to a mol % of methanol that is converted, is at least 30%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
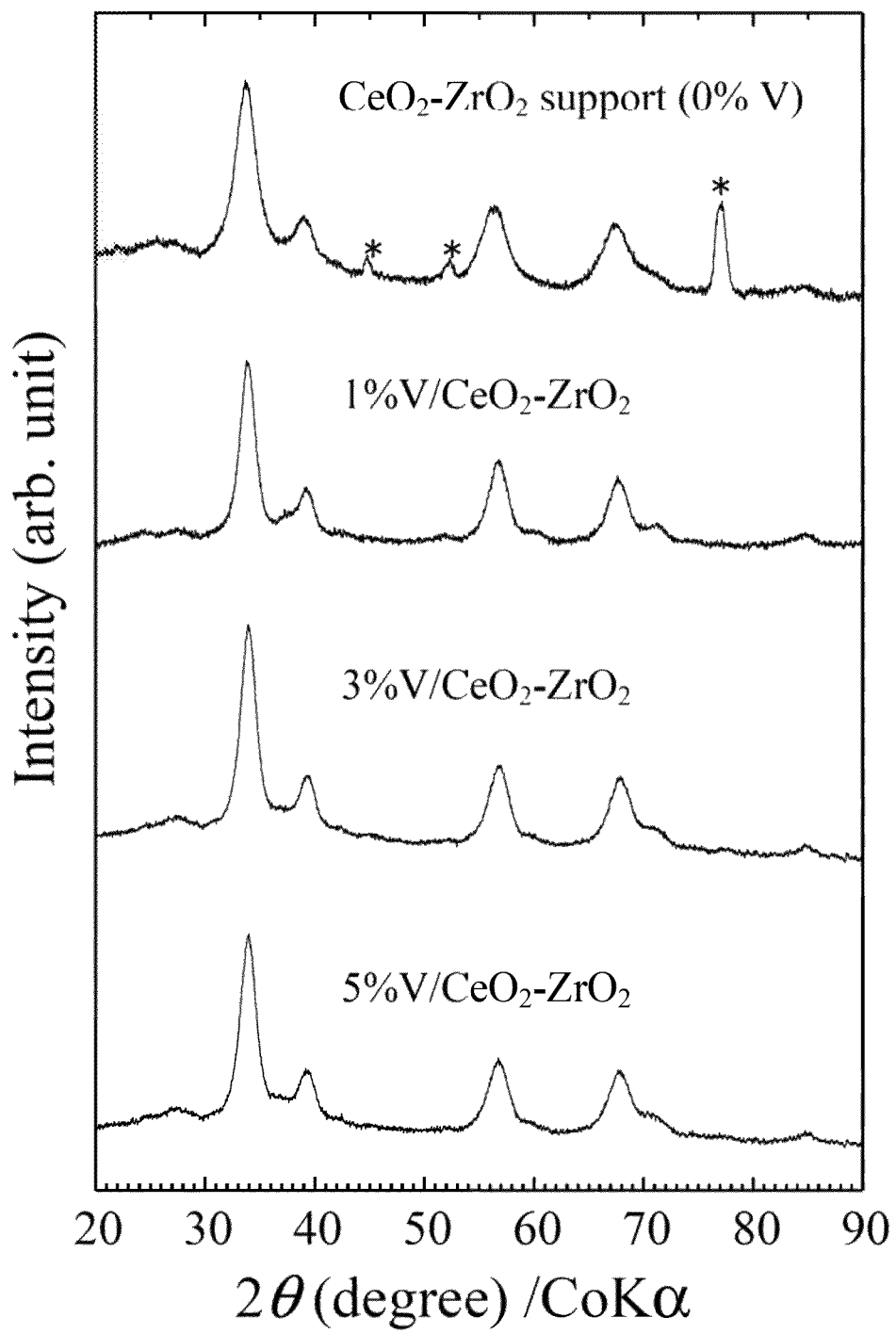
FIG. 1 shows X-ray diffraction (XRD) patterns of a $CeO_2$-$ZrO_2$ support with 0% vanadium, a 1% V/$CeO_2$-$ZrO_2$ catalyst, a 3% V/$CeO_2$-$ZrO_2$ catalyst, and a 5% V/$CeO_2$-$ZrO_2$ catalyst.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "the catalyst" refers to the $CeO_2$ and $ZrO_2$ supported vanadium oxide catalyst of the First aspect of the disclosure, unless otherwise indicated.

According to a first aspect, the present disclosure relates to a $CeO_2$ and $ZrO_2$ supported vanadium oxide catalyst. The catalyst comprises 0.1-10 wt % vanadium (V), preferably 0.5-8 wt % vanadium, more preferably 1-5 wt % vanadium;

65-80 wt % $CeO_2$, preferably 65-75 wt % $CeO_2$, more preferably 65-70 wt % $CeO_2$; and 20-32 wt % $ZrO_2$, preferably 22-31 wt % $ZrO_2$, more preferably 25-30 wt % $ZrO_2$. Additionally, the $CeO_2$ and $ZrO_2$ supported vanadium oxide catalyst may be referenced by "x % $V/CeO_2$-$ZrO_2$," where x % is the weight percent of vanadium per total weight of the catalyst. The vanadium oxide may comprise VO (vanadium(II) oxide), $V_2O_3$ (vanadium(III) oxide), $VO_2$ (vanadium(IV) oxide), and/or $V_2O_5$ (vanadium(V) oxide, or vanadia). The vanadium oxide may also comprise distinct phases such as $V_3O_7$, $V_4O_9$, $V_6O_{13}$, and Magnéli phases such as $V_4O_7$, $V_5O_9$, $V_6O_{11}$, $V_7O_{13}$, and $V_8O_{15}$. In one embodiment, the vanadium oxide comprises a majority of $V_2O_5$, for example, 70-100 mol %, preferably 80-100 mol %, more preferably 90-100 mol % of the total vanadium in the catalyst is present as $V_2O_5$. In one preferred embodiment, all of the vanadium oxide in the catalyst is $V_2O_5$. In an alternative embodiment, the catalyst may comprise greater than 10 wt % vanadium, for example, 10-50 wt % or 20-40 wt %.

In one embodiment, the catalyst has a Ce to Zr molar ratio of 1.4:1-3.5:1, preferably 1.5:1-3.1:1, more preferably 1.6:1-2.0:1. The catalyst may be in the form of a composite. As defined here, a composite refers to a combination of two or more distinct constituent materials into one solid object, such as a particle, where the individual constituent materials, on an atomic level, remain separate and distinct within the finished structure. Here, the distinct constituent materials comprise $CeO_2$, $ZrO_2$, and vanadium oxide. In some embodiments, different forms or phases of vanadium oxide may be considered distinct constituent materials. Where the catalyst is in the form of a composite, it may be a nanocomposite, where one of the constituent materials or phases has one, two, or three dimensions of less than 100 nanometers, or structures having nanoscale repeat distances between the different phases that make up the material. In another embodiment, the catalyst may have domains of constituent materials or phases that are larger than a nanocomposite, for example, where the dimension or structure of a constituent material or phase is about 100 nm-40 µm, preferably 400 nm-10 µm, or 500 nm-1 µm.

In one embodiment, the catalyst may comprise additional components/compounds. These components/compounds may be those with catalytic properties such as titanium oxide, molybdenum oxide, a zeolite, copper, zinc oxide, silver, platinum, nickel, palladium, or polyaniline, and may be present in an amount of 0.1-14.5 wt %, preferably 1-10 wt %, more preferably 2-6 wt % relative to the total weight of the catalyst. Alternatively, an additional component/compound may function as a support, such as silica, alumina, potassium oxide, or magnesium chloride, and may be present in an amount of 0.1-14.5 wt %, preferably 1-10 wt %, more preferably 2-6 wt % relative to the total weight of the catalyst, though in alternative embodiments, may be present at a higher weight percent. In some embodiments, a component/compound may be considered a support but also exhibit catalytic activity, such as titanium dioxide. In alternative embodiments, a support may have a substantially larger mass, such as a porous fused silica disc having a height of 5-10 mm and a diameter of 3-5 mm, and decorated with composite particles comprising $CeO_2$, $ZrO_2$, and vanadium oxide. In this alternative embodiment, the decorated disc may be considered the catalyst.

In one embodiment, the catalyst is in the form of microparticles with diameters of 50-200 µm, preferably 70-150 µm, more preferably 80-100 µm. In a related embodiment, the microparticles may have a composite core of $CeO_2$ and $ZrO_2$ with vanadium oxide nanoparticles decorated on the surface, where the vanadium oxide nanoparticles have diameters of 1-100 nm, preferably 2-50 nm, more preferably 2-20 nm. In one embodiment, the microparticles may have a composite core of $CeO_2$ and $ZrO_2$ with nanoscale domains of vanadium oxide disposed within, having diameters similar to those mentioned for vanadium oxide nanoparticles. In another related embodiment, the microparticles may have a composite core of $CeO_2$ and $ZrO_2$ with both vanadium oxide nanoparticles decorated on the surface and vanadium oxide nanoscale domains disposed within the core. In this embodiment, preferably at least 30%, more preferably at least 50% of the vanadium oxide nanoparticles and vanadium oxide nanoscale domains out of the total number of individual vanadium oxide nanoparticles and vanadium oxide nanoscale domains have at least one exposed surface. Preferably out of the total exposed surface area of a composite catalyst particle, 0.5-10%, more preferably 1-8% of the exposed surface area of the particle is a surface of vanadium oxide. In an alternative embodiment, the catalyst may comprise particles with core-shell structures, such as a $CeO_2$ and $ZrO_2$ composite core surrounded by a vanadium oxide shell that covers greater than 80%, preferably greater than 90%, more preferably greater than 98% of the composite core's surface area. In this alternative embodiment, the catalyst comprises greater than 10 wt % vanadium.

In one embodiment, the catalyst has a surface area of 80-150 m²/g, preferably 90-130 m²/g, more preferably 95-120 m²/g. The surface area may be determined by mercury porosimetry, Brunauer-Emmett-Teller (BET) analysis of low temperature $N_2$ adsorption isotherms, or some other technique. Preferably the surface area is determined by BET analysis of $N_2$ adsorption isotherms. In one embodiment, the catalyst may be a porous material, having pore sizes of 1-100 nm, preferably 2-40 nm, more preferably 3-20 nm.

The catalyst may have physical or chemical properties that are different than individual components of $CeO_2$, $ZrO_2$, and vanadium oxide. For example, the percent methanol conversion of the oxidative dehydration may be higher with the catalyst, than with a mixture of individual particles each of $CeO_2$, $ZrO_2$, and vanadium oxide at similar wt % ratios as those described for the composite material.

According to a second aspect, the present disclosure relates to a method for producing the $CeO_2$ and $ZrO_2$ supported vanadium oxide catalyst of the first aspect. This method involves mixing a $CeO_2$ powder, a $ZrO_2$ powder, a vanadium compound, and water to form a solution; drying the solution to produce a dried catalyst precursor; heating the dried catalyst precursor at 450-700° C. for 2-8 hours to produce a calcined powder; and pelletizing and grinding the calcined powder to produce the $CeO_2$ and $ZrO_2$ supported vanadium oxide catalyst. The obtained catalyst might be shaped using well known methods used in laboratories and industry. This method may be considered a wetness impregnation technique, wherein the support (or carrier) is contacted (or impregnated) with a solution of dissolved metal oxide precursor (in one embodiment, ammonium metavanadate).

In one embodiment of the method, the vanadium compound is one selected from the group consisting of ammonium metavanadate, potassium metavanadate, sodium metavanadate, bismuth vanadate, vanadium oxytrichloride, vanadium pentafluoride, and vanadium oxide. In alternative embodiments, the vanadium compound may be vanadium metal, sodium decavanadate, sodium orthovanadate, yttrium orthovanadate, vanadium carbide, vanadium hexacarbonyl, vanadium nitride, vanadium phosphate, vanadium tetrachloride, vanadium tetrafluoride, vanadium-gallium, vanadium(II) bromide, vanadium(II) chloride, vanadium(III) bromide, vanadium(III) chloride, vanadium(III) fluoride, vanadium (III) iodide, vanadium(III) sulfate, vanadium(V) oxytrifluoride, vanadium(III) acetylacetonate, vanadyl acetylacetonate, vanadyl nitrate, vanadyl perchlorate, or vanadyl sulfate. Where the vanadium compound is vanadium oxide, it may be in any of the formulas as mentioned previously.

In one embodiment, the solution of $CeO_2$ powder, $ZrO_2$ powder, vanadium compound, and water has a vanadium concentration of 0.05-1.0 M, preferably 0.05-0.5 M, more preferably 0.08-0.2 M. Alternatively, the vanadium compound may be added to a certain weight percentage of the solution, for example, 0.01-10 wt % of the total solution, preferably 0.1-5 wt %, more preferably 0.5-2 wt %. In one embodiment, the vanadium compound is ammonium metavanadate ($NH_4VO_3$). In this embodiment, the ammonium metavanadate may be mixed or dissolved to form a first aqueous solution comprising 0.5-2 wt % vanadium oxide or vanadate ion. Alternatively, 10-13 g, preferably 11-12 g ammonium metavanadate may be dissolved per every L of water in this first aqueous solution. To increase the solubility of the ammonium metavanadate, the first aqueous solution may be heated to 35-50° C., preferably 37-45° C., while stirring or agitating.

The $CeO_2$ and $ZrO_2$ powders may comprise particles of $CeO_2$ and $ZrO_2$ having diameters of 20 nm-100 μm, preferably of 50 nm-10 μm, more preferably 100 nm-5 μm. In one embodiment, the $CeO_2$ and $ZrO_2$ powders may be premixed before mixing with water or the first aqueous solution. In an alternative embodiment, the $CeO_2$ and $ZrO_2$ powders may comprise one or more particles containing both $CeO_2$ and $ZrO_2$, at a Ce:Zr molar ratio of 1:10-10:1, preferably 1:5-5:1, more preferably 1:4-4:1. In another embodiment, particles of the $CeO_2$ and $ZrO_2$ powders may have surface areas of 10-200 $m^2/g$, preferably 20-150 $m^2/g$, more preferably 50-120 $m^2/g$. In one embodiment, the powders are mixed to have a $CeO_2$:$ZrO_2$ mass ratio of 2.0:1-4.0:1, preferably 2.5:1-3.5:1, more preferably 2.7:1-3.3:1. Alternatively, the $CeO_2$ and $ZrO_2$ powders may be mixed to result in a Ce to Zr molar ratio as mentioned previously for the catalyst. The powders may be mixed by stirring, shaking, folding, blending, blowing, spraying, or grinding. In an alternative embodiment, $CeO_2$ and/or $ZrO_2$ nanoparticles having diameters of less than 30 nm, or less than 20 nm, and suspended in water or some other solution, may be used in place of one or both powders.

Preferably, the $CeO_2$ and $ZrO_2$ powders are mixed before being added to the vanadium compound, but in one embodiment, a separate $CeO_2$ powder and a separate $ZrO_2$ powder may be mixed sequentially into the first aqueous solution, or may mixed sequentially into a volume of water, which is then mixed with the first aqueous solution. Alternatively, the vanadium compound may be mixed with either $CeO_2$ or $ZrO_2$ separately, and then mixed with the remaining oxide, or the vanadium compound may be mixed last into a mixture of both $CeO_2$ and $ZrO_2$ in water. In a preferred embodiment, the mixture of $CeO_2$ and $ZrO_2$ powders is mixed into the first aqueous solution of the vanadium compound in water to result in a $CeO_2$ and $ZrO_2$ weight percentage of 25-40 wt %, preferably 30-35 wt % of the total solution. In one embodiment, the solution of the $CeO_2$, $ZrO_2$, vanadium compound, and water may be sonicated or heated to increase the particle dispersion or dissolution.

The solution of the $CeO_2$, $ZrO_2$, vanadium compound, and water may then be dried by spray-drying, freeze drying, evaporation at ambient conditions, evaporation in a desiccator, evaporation in an oven, evaporation under a stream of inert gas such as $N_2$ or Ar, and/or evaporation under a vacuum. In one embodiment, the solution is evaporated in a rotary vacuum evaporator operating at a temperature of 32-55° C., preferably 35-50° C., more preferably 38-45° C., and at an absolute pressure of 10-100 mbar, preferably 20-80 mbar, more preferably 30-70 mbar. The solution may optionally be filtered before the drying, in order to quickly separate the Ce, Zr, and vanadium solid compounds from the solution and reduce the drying time. Alternatively, the solution may be partially evaporated in a rotary vacuum evaporator and then filtered.

A dried catalyst precursor may be further dried in an oven at 70-150° C., preferably 80-130° C., more preferably 100-120° C., for 1-5 h, preferably 2-4 h. The powder may then be calcined by heating at 450-700° C., preferably 450-600° C., more preferably 475-525° C. in static air for 2-8 h, preferably 2-6 h, more preferably 2.5-3.5 h. Between the oven drying and the calcination, the powder may be allowed to cool below 70-150° C., or may be allowed to cool to room temperature. Alternatively, the dried catalyst precursor may not be cooled between the oven drying and the calcination. For example, the dried catalyst precursor may be heated at 70-150° C. in an oven, and then the temperature of the oven may be increased to 450-700° C. to calcine the dried catalyst precursor. In another embodiment, the dried catalyst precursor may be removed from the drying oven and immediately placed in a second oven preheated to 450-700° C. for the calcination. In one embodiment of the method, after the oven drying, the dried catalyst precursor is allowed to cool to a temperature of 20-35° C., preferably 22-32° C., more preferably 20-30° C., preferably by sitting at room temperature, and is then placed in an oven having an equivalent temperature, or a temperature of 20-35° C. The oven temperature may then be increased at a rate of 3-6° C./min, preferably 4-6° C./min, more preferably about 5° C./min to reach a previously mentioned calcination temperature. In an alternative embodiment, the dried catalyst precursor may undergo the calcination without the previously mentioned 70-150° C. oven drying step. In one embodiment, the calcination may be required to fix the vanadium oxide onto the $CeO_2$ and $ZrO_2$ support, and may lead to the formation of mixed oxide compounds.

Following the calcination, the oven may be turned off and allowed to cool to room temperature, or the calcined powder may be removed and allowed to cool to room temperature.

In one embodiment, the calcined powder is pelletized, ground and sieved to produce the catalyst of uniform diameter. The pelletizing may produce pellets which are defined here as self-sustaining solids that retain at least 25% of the surface area per mass of the starting calcined powder. The pelletizing may be done with a rotary drum pelletizer, a pan pelletizer, or a pellet press, and the calcined sample may be subjected to pressures of 50-6,000 psi, preferably 100-5,000 psi, more preferably 500-3,000 psi. The pellets may have a longest diameter of 3-20 mm, preferably 4-15 mm, and a shortest diameter of 1-10 mm, preferably 2-8 mm. Preferably the pellets are formed in a prismatic shape, such as a cylinder or a rectangular prism, though in other embodiments, the pellets may be formed into spherical or hemispherical shapes.

In another embodiment, the calcined powder may be pressed together into one single solid, such as a disc or cylinder, rather than individual pellets. The grinding may be with a mortar and pestle, a burr mill, a blade grinder, sandpaper, a ball mill, a disc mill, a jet mill, a conical mill, a hammer mill, or some other milling or grinding machine.

Preferably, the pelletizing and grinding is performed in order to increase the population of particles having a particle size between 50-200 µm, preferably 70-150 µm, more preferably 80-100 µm, as mentioned previously for the catalyst. However, the pelletizing and grinding may be carried out to produce particles having some other size range, shape, or to change the average surface area of the powder. In one embodiment, the calcined powder may be screened through a mesh or sieve to select for catalyst particles having a certain size, without the step of pelletizing and grinding. In another embodiment, the calcined powder may have an average particle size that is larger than desired, and thus may be ground and screened for a particle size range without a step of pelletizing. In another embodiment, catalyst particles larger or smaller than a certain particle size range may be repeatedly pelletized and/or ground. The screening or sieving of the particles may include a vibrating screen, a gyrating screen, a trommel screen, or some other mechanical separation device.

In an alternative embodiment, prior to the pelletizing, a binding agent or binder may be added to the catalyst powder. This binder may inhibit the interaction of contaminants in the reactor with the catalyst. The binder may form an aggregate with the catalyst, enhance the catalyst's temperature and/or mechanical stability, or provide a specified structure for the catalyst to take a shape. The binder may be a cellulosic polymer, a resin, calcium phosphate, or a combination thereof, and may have weight percent of 1-80 wt %, preferably 5-50 wt %, more preferably 10-30 wt % within the catalyst. For example, an organic thermoplastic resin binder may be employed to form a porous matrix for the catalyst in a small particle or pellet form. A cellulosic polymer may be used to provide a disordered porous fiber on which the catalyst may be distributed. With certain binders in use, pellets may be formed with less than 50 psi pressure applied, or with almost no pressure applied. In an alternative embodiment, $CeO_2$ powder, $ZrO_2$ powder, and a vanadium compound may be mixed together and pelletized, without the step of dissolving in water, drying, or calcining.

According to a third aspect, the present disclosure relates to a method of dehydrating methanol into dimethyl ether. This method involves feeding a gas stream comprising $O_2$ and methanol to a fixed bed flow reactor comprising the $CeO_2$ and $ZrO_2$ supported vanadium oxide catalyst to produce dimethyl ether and at least one side product selected from the group consisting of hydrogen gas, carbon monoxide, carbon dioxide, water, and formaldehyde.

In one embodiment, the gas stream is fed to the fixed bed flow reactor at a flowrate of 40-60 $cm^3$/min, preferably 42-58 $cm^3$/min, more preferably 45-55 $cm^3$/min per 0.1 g of the $CeO_2$ and $ZrO_2$ supported vanadium oxide catalyst. In one embodiment, the gas stream has an $O_2$ to methanol molar ratio of 0.2:1-0.6:1, preferably 0.25:1-0.55:1, more preferably 0.28:1-0.52:1. In one embodiment, the gas stream further comprises 60-85 vol %, preferably 65-80 vol,%, more preferably 70-80 vol % of an inert carrier gas relative to the total volume of the gas stream. Preferably the inert gas is helium, argon, or nitrogen, though in other embodiments the gas may be any gas that is not reacted or converted, and preferably does not affect the catalytic process beyond changing flowrates or concentrations. In an alternative embodiment, a carrier gas may be used that is the same species as one of the products of the oxidative reduction of methanol, for example, $CO_2$. In another alternative embodiment, the gas stream fed to the fixed bed flow reactor consists of only $O_2$ and methanol without a carrier gas. Before entering the fixed bed flow reactor, the gas stream may be heated to 100-200° C., preferably 120-180° C., more preferably 140-160° C.

Before receiving the gas stream, the fixed bed flow reactor may be heated at 100-180° C., preferably 120-170° C., more preferably 140-160° C., for 0.5-6 h, preferably 0.5-3 h, more preferably 0.5-1.5 h. Prior to the reaction, the fixed bed flow reactor may be heated to a reaction temperature of 200-375° C., preferably 200-300° C., more preferably 225-300° C. The fixed bed flow reactor may reach this reaction temperature by increasing its internal temperature at a rate of 2-8° C./min, preferably 3-7° C./min, more preferably 4-6° C./min.

In one embodiment, the gas stream is fed to the fixed bed flow reactor at a gas hourly space velocity of 25,000-35,000 $h^{-1}$, preferably 27,000-33,000 $h^{-1}$, more preferably 28,000-32,000 $h^{-1}$. In one embodiment, the absolute pressure of the gas stream in the fixed bed flow reactor may be 0.5-1.5 atm, preferably 0.7-1.4 atm, more preferably 0.8-1.2 atm.

Contacting the catalyst with the gas stream at the reaction temperature may result in a conversion of the methanol and $O_2$ reactants into gas phase products such as DME, CO, $CO_2$, $H_2$, $H_2O$, and/or formaldehyde. The flow of the gas stream allows the displacement of the gas phase products and unconverted methanol and $O_2$. These species can then be separated by one or more molecular sieve, adsorbent, or trapping agent and analyzed to determine concentrations. The molecular sieve, adsorbent, or trapping agent may be carbon based adsorbents, such as activated carbon, charcoal, or the Carbopak® series, porous polymers, such as the Chromosorb® series, the Porapak® series, the Tenax® series, the HayeSep® series, the XAD® series, clays, diatomaceous earth, magnesium silicates, such as Florisil®, ashes, micronized silicon dioxide, chrislobalite, hydrated sodium calcium aluminosilicates, chitosan, granulas, anionic ion exchange resins, cationic ion exchange resins, modified ion exchange resins, zeolites, perlite, bentonoite, C4-30 aliphatic hydrocarbons, C4-30 unsaturated hydrocarbons, gas chromatography stationary phases, liquid chromatography stationary phases, polyethylene glycol with a melting point in the range from 30 to 100° C., preferably 40 to 50° C., silica gel, aluminum oxide, cellulose, granulates, high boiling liquids such as polysiloxanes, phenyl substituted stationary phases, bases, acids, and diethylene glycol succinate derivatives. The powder forms of molecular sieves may be of type 3A, 4A, 5A, and 13X. Following separation, a GCMS, such as an HP G1540A, or a mass spectrometer may be used to determine concentrations. Alternatively, a GCMS may be used without a molecular sieve or without prior separation of the products. In an alternative embodiment, the exit gas stream may be condensed to form a liquid mixture, which is then analyzed. In one embodiment, before the exit gas stream is analyzed, the reaction may be allowed to run for 1-6 h, preferably 2-4 h, more preferably 2.5-3.5 h at specific reaction conditions so that the reaction products achieve steady state concentrations.

In other embodiments, a distillation column or distillation tower may be used to separate or purify DME. The distillation column may be a fractionating column, and the distillation column may be used in a continuous or batch distillation process. Other separation processes may be used, such as fractional freezing.

The success of the reaction may be determined by the percent conversion of the reactants, the percent selectivity of the gas phase products, and/or the percent yield of the gas phase products. Based on these values, a person having ordinary skill in the art may be able to determine preferable reaction parameters.

The percentage conversion of a reactant is a mol % of the reactant converted into one or more products, based on the total reactant fed to the reactor. This may be determined by subtracting the unreacted amount of reactant (such as $CH_3OH_{out}$) from the total amount of reactant fed (such as $CH_3OH_{in}$), dividing by the total amount of reactant fed, and converting to a percentage. The conversion percentages for methanol ($CH_3OH$) and $O_2$ are then:

$$CH_3OH \text{ conversion}(\%) = \frac{\text{mol } CH_3OH_{in} - \text{mol } CH_3OH_{out}}{\text{mol } CH_3OH_{in}} \times 100$$

$$O_2 \text{ conversion}(\%) = \frac{\text{mol } O_{2_{in}} - \text{mol } O_{2_{out}}}{\text{mol } O_{2_{in}}} \times 100$$

Figure 13:
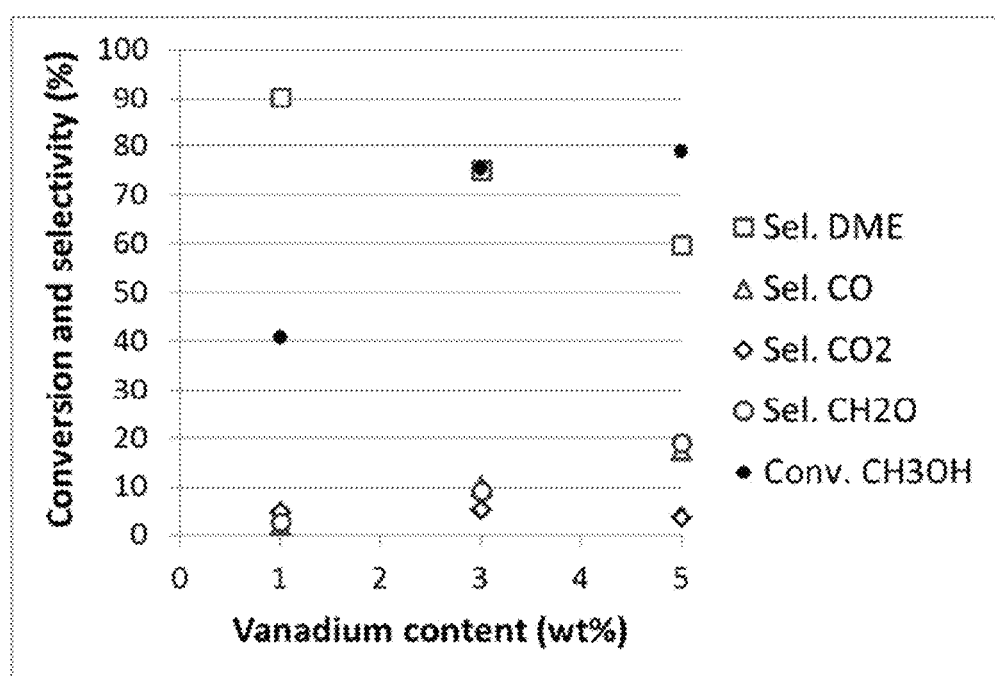
FIG. 13 shows methanol conversion and product selectivities obtained using a 1%, 3%, and 5% V/$CeO_2$-$ZrO_2$ catalyst at 250° C. and at an $O_2$/$CH_3OH$ molar ratio of 0.5.

FIGS. 2-7 show example conversion percentages of methanol and $O_2$ using a 1% $V/CeO_2$-$ZrO_2$ catalyst at temperatures of 200-350° C. and at $O_2$ to methanol molar ratios ranging from 0:1 (i.e., no $O_2$) to 0.5:1. With $O_2$ to methanol molar ratios of 0.3:1-0.5:1, the conversion percentages of methanol and $O_2$ are generally higher at higher temperatures. FIG. 13 shows that at 250° C. and at an $O_2$ to methanol molar ratio of 0.5:1, increasing the vanadium content from 1 wt % to 5 wt % increases the conversion of methanol.

In one embodiment, at least 35 mol % of the methanol is converted to dimethyl ether and at least one side product selected from the group consisting of hydrogen gas, carbon monoxide, carbon dioxide, water, and formaldehyde. In other words, the percentage conversion of methanol is at least 35%. In one embodiment, a percentage conversion of methanol of at least 35% may occur at reaction conditions of 250° C. with an $O_2$ to methanol molar ratio of 0.5:1, and with a catalyst having a vanadium content from 1 wt % to 5 wt%, as shown in FIGS. 10-13. The at least 35% methanol conversion may also occur with the 1% $V/CeO_2$-$ZrO_2$ catalyst at reaction temperatures of 250° C. and higher with $O_2$ to methanol molar ratios of 0.2:1-0.5:1, as shown in FIGS. 4-7 and 9. In some embodiments, preferably the conversion of methanol is greater than 40% or greater than 50%.

The selectivity of a gas phase product is a stoichiometric mol. % of the product produced per mol of a reactant converted or consumed. Here, the selectivities are based on the mol methanol converted or consumed, which is $CH_3OH_{in}$-$CH_3OH_{out}$, as expressed within the previous equations. A product having a selectivity of exactly 100% means that all of the reactant that was consumed went into a stoichiometric equivalent of that particular product. For example, in the catalytic process of the current invention, a DME selectivity of 100% means that every mol of methanol converted leads to a ½ mol of DME produced. The stoichiometric factor of ½ is used given that methanol has one carbon per molecule, while DME has two. A product having a selectivity of exactly 0% means than none of the product was produced, regardless of whether or not reactant is converted. The percentage conversions for the products are:

$$CH_2O \text{ selectivity}(\%) = \frac{\text{mol } CH_2O}{\text{mol of } CH_3OH_{consumed}} \times 100$$

$$CO \text{ selectivity}(\%) = \frac{\text{mol } CO}{\text{mol of } CH_3OH_{consumed}} \times 100$$

$$CO_2 \text{ selectivity}(\%) = \frac{\text{mol } CO_2}{\text{mol of } CH_3OH_{consumed}} \times 100$$

$$H_2 \text{ selectivity}(\%) = \frac{\frac{1}{2}\text{mol } H_2}{\text{mol of } CH_3OH_{consumed}} \times 100$$

$$DME(CH_3OCH_3) \text{ selectivity}(\%) = \frac{2 \times \text{mol } DME}{\text{mol of } CH_3OH_{consumed}} \times 100$$

In addition, a selectivity for a particular product may be expressed in terms of the production of other products. For instance, a molar balance of C for the reactor is shown by:

mol $C_{in}$=mol $C_{out}$.

By substituting the carbon-containing reactants and products, the balance becomes:

mol $CH_3OH_{in}$=mol $CH_3OH_{out}$+mol $CH_2O$+mol CO+mol $CO_2$+½(mol DME).

Writing in terms of mol DME:

mol DME=2(mol. $CH_3OH_{in}$−(mol $CH_3OH_{out}$+mol $CH_2O$+mol CO+mol $CO_2$)).

Then, the DME selectivity may be written in terms of the $CH_3OH$ and the other carbon-containing products:

$$DME(CH_3OCH_3) \text{ selectivity}(\%) = \frac{\text{mol. } CH_3OH_{in} - (\text{mol } CH_3OH_{out} + \text{mol } CH_2O + \text{mol } CO + \text{mol } CO_2)}{\text{mol } CH_3OH_{consumed}} \times 100.$$

Thus, the DME selectivity may be determined without a direct measurement of the DME produced.

Figure 9:
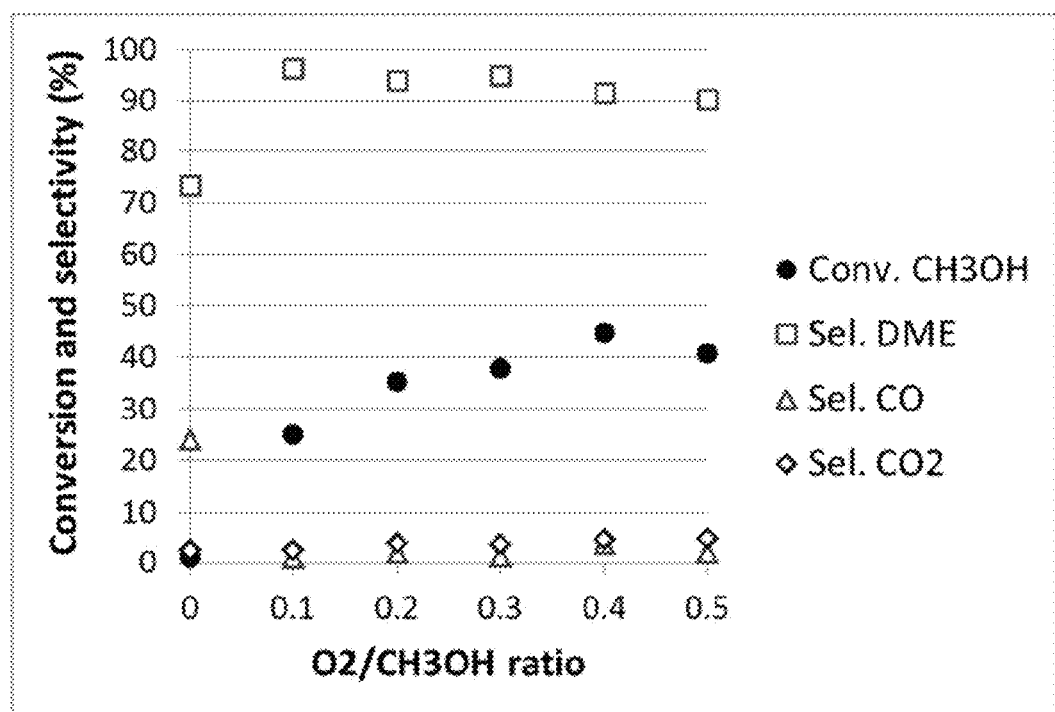
FIG. 9 shows methanol conversions and product selectivities obtained using a 1% V/$CeO_2$-$ZrO_2$ catalyst at 250° C. and over $O_2$/$CH_3OH$ molar ratios of 0-0.5.

FIGS. 2-7 show example selectivities of $H_2$, CO, $CO_2$, $CH_2O$, and DME using a 1% $V/CeO_2$-$ZrO_2$ catalyst at temperatures of 200-350° C. and $O_2$ to methanol molar ratios ranging from 0:1 (i.e., no $O_2$) to 0.5:1. Over this temperature range, the selectivity of DME tends to decrease at higher temperatures, while the selectivities of CO and $CO_2$ tend to increase. FIG. 9 shows that for the 1% $V/CeO_2$-$ZrO_2$ catalyst at 250° C., the selectivities of DME, CO, and $CO_2$ do not change appreciably over $O_2$ to methanol molar ratios of 0.1:1-30.5:1. FIG. 13 shows that at 250° C. and an $O_2$ to methanol molar ratio of 0.5:1, increasing the vanadium content from 1 wt % to 5 wt % decreases the selectivity of DME and increases the selectivity of CO and $CH_2O$.

In one embodiment, a selectivity percentage for dimethyl ether from the conversion of methanol is at least 90%. In one embodiment, this may occur at reaction conditions of 200-250° C. with $O_2$ to methanol molar ratios of 0.1:1-0.5:1 when using a 1% $V/CeO_2$-$ZrO_2$ catalyst, as shown in FIGS. 3-7 and 9. In some embodiments, the selectivity of dimethyl ether may be at least 92% or at least 95%. Preferably the selectivities of other products, such as $H_2$, CO, $CO_2$, and $CH_2O$, are 0-20%, more preferably 0-10%.

The amount of a product produced may be further described by a percentage yield. This value represents the mol % yield for a product based on the total mol of a reactant entering the reactor. A product having a percentage yield of 100% requires that both the reactant conversion percentage and the product selectivity percentage equal 100%, meaning that all of the reactant entering the reactor reacts to produce the product. The percentage yield of a product is found by multiplying the reactant conversion percentage by the product selectivity percentage, and dividing by 100. For instance, the percentage yield of DME for the reaction is:

$$DME\ yield(\%) = \frac{CH_3OH\ conversion(\%) \times DME\ selectivity(\%)}{100}$$

Figure 8:
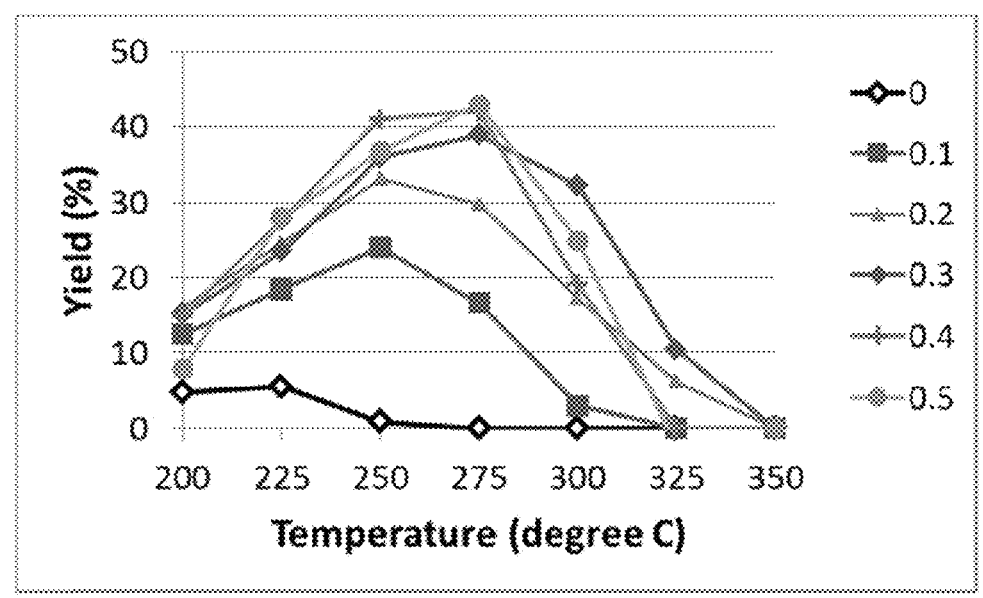
FIG. 8 shows dimethyl ether percentage yields obtained using the 1% V/$CeO_2$-$ZrO_2$ catalyst over $O_2$/$CH_3OH$ molar ratios of 0-0.5 and over a temperature range of 200-350° C.
Figure 12:
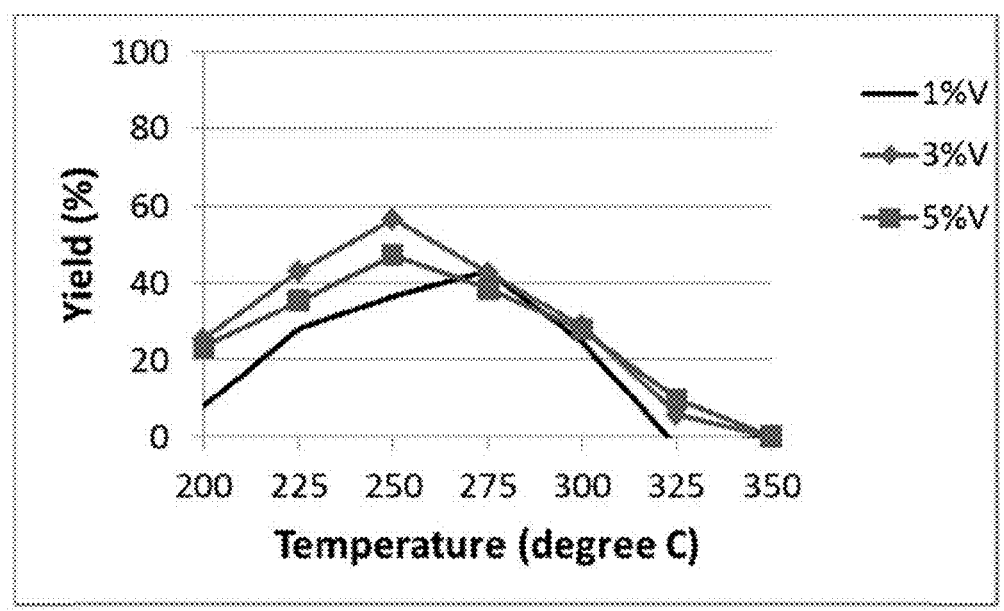
FIG. 12 shows dimethyl ether percentage yields obtained using a 1%, 3%, and 5% V/$CeO_2$-$ZrO_2$ catalyst with an $O_2$/$CH_3OH$ molar ratio of 0.5 and over a temperature range of 200-350° C.

FIG. 8 shows example DME percentage yields using a 1% $V/CeO_2-ZrO_2$ catalyst at temperatures of 200-350° C. and $O_2$ to methanol molar ratios ranging from 0:1 (i.e., no $O_2$) to 0.5:1. Here, the DME percentage yield peaks at temperatures of 250° C. and 275° C. for $O_2$ to methanol molar ratios of 0.4:1 and 0.5:1. FIG. 12 also shows peak DME percentage yields for 1% $V/CeO_2-ZrO_2$, 3% $V/CeO_2-ZrO_2$, and 5% $V/CeO_2-ZrO_2$ catalysts at 250 and 275° C. at an $O_2$ to methanol molar ratio of 0.5:1. The peak DME percentage yields at the moderate temperatures result from the DME selectivity being high at low temperatures and low at high temperatures, while the methanol conversion exhibits the opposite behavior.

In one embodiment, a percentage yield of dimethyl ether, relative to a mol % of methanol that is converted, is at least 30%. In one embodiment, this may occur at reaction conditions of 250-300° C., preferably 250-275° C. with $O_2$ to methanol molar ratios of 0.2:1-0.5:1, preferably 0.3:1-0.5:1 when using a 1% $V/CeO_2-ZrO_2$ catalyst, as shown in FIG. 8. With these conditions, the DME percentage yield may be greater than 35% or even greater than 40%.

In another further embodiment, a percentage yield of dimethyl ether, relative to a mol % of methanol that is converted, is at least 50%. In one embodiment, this may occur at reaction conditions of 237-262° C., preferably 245-255° C. with a 2%-4% $V/CeO_2-ZrO_2$, preferably with a 3% $V/CeO_2-ZrO_2$ catalyst, and with an $O_2$ to methanol molar ratio of 0.4:1-0.5:1, preferably about 0.5:1, as shown in FIG. 12. In other embodiments, the percentage yield of dimethyl ether may be at least 55% or at least 60%.

Figure 14:
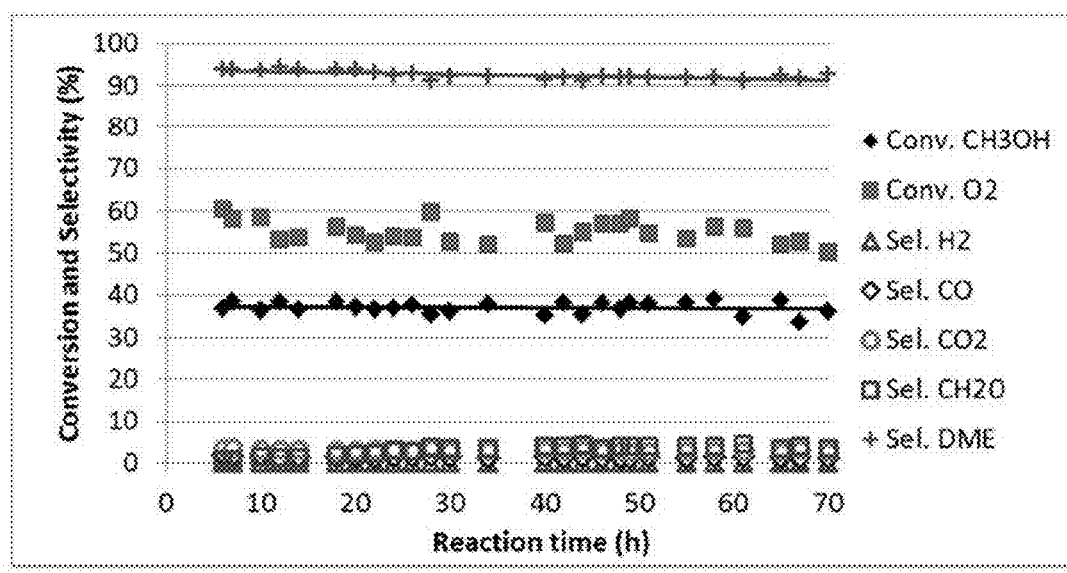
FIG. 14 shows the stability of reactant conversions and product selectivities over a 70 hour reaction period for a 1% V/$CeO_2$-$ZrO_2$ catalyst at 250° C. being exposed to an $O_2$/$CH_3OH$ molar ratio of 0.3.

The catalyst reaction may enable the methanol oxidative reaction to continue at a stable reaction rate for several hours. For a fixed flow rate of the gas stream, a fixed temperature, and a fixed $O_2$ to methanol molar ratio, the stability of the reaction rate may be judged by monitoring a reactant conversion, a product selectivity, and/or a product yield over a period of time. In one embodiment, a percentage yield of dimethyl ether, relative to a mol % of methanol that is converted, is maintained at a value of at least 30%, preferably at least 32%, more preferably at least 34% for a reaction period of at least 50 hours, preferably at least 60 hours, more preferably at least 70 hours. In a further embodiment, over this reaction period, the selectivity of DME may be maintained at a value of at least 90%, preferably at least 91%, while the conversion of methanol may be maintained a value of at least 30%, preferably at least 32%, more preferably at least 35%. In one embodiment, this stable reaction rate may occur at reaction conditions of 230-300° C., preferably 230-270° C., more preferably 240-260° C. with $O_2$ to methanol molar ratios of 0.2:1-0.5:1, preferably 0.2:1-0.4:1, more preferably about 0.3:1 when using a 1% $V/CeO_2-ZrO_2$ catalyst, for example, as shown in FIG. 14. Alternatively, a DME percentage yield of at least 50% may be maintained for 50 h or more using the reaction conditions mentioned above in the previous paragraph.

The examples below are intended to further illustrate protocols for preparing, characterizing, and using the $CeO_2$ and $ZrO_2$ supported vanadium oxide catalyst, and are not intended to limit the scope of the claims.

EXAMPLE 1

Preparation of $V/CeO_2-ZrO_2$ Catalyst

A mixture of $CeO_2$ and $ZrO_2$ was prepared by mechanical mixing of their corresponding fine powders with a gravimetric ratio of $CeO_2$:$ZrO_2$=3:1.

Vanadium oxide was deposited on a $CeO_2-ZrO_2$ support by an incipient wetness impregnation method. To prepare 5 g of 1 wt % V supported on $CeO_2-ZrO_2$ catalyst, 0.1171 g of ammonium metavanadate ($NH_4VO_3$, Aldrich, U.S.A., >99%) was dissolved in 10 mL of deionized water at 40° C., resulting in a faint orange transparent solution. 5 g of the $V/CeO_2-ZrO_2$ prepared by mechanical mixing as described above was then added to the vanadium aqueous solution. Water was then evaporated using a rotary evaporator operating at 40° C. and 40-60 mbar. The resulting powder was then collected and dried in an oven at 110° C. for 3 h. The powder was then calcined in static air at 500° C. for 5 h. The desired temperature was attained by increasing the oven temperature from 25° C. to 500° C. with a ramping rate of 5° C. min$^{-1}$.

The obtained powder was then pelletized, and the pellets were grounded. A fraction of the grounded material with particle sizes between 0.08 and 0.1 mm was selected and used for catalytic activity and selectivity measurements.

3 wt % and 5 wt % V supported on $CeO_2-ZrO_2$ catalysts were also prepared by a similar procedure.

EXAMPLE 2

Characterization of the Catalysts

Crystal structure of the prepared catalysts was characterized by X-ray diffraction (XRD, Equinox 1000, INEL, France) using filtered Co-Kα1 radiation. FIG. 1 shows the XRD patterns of four different samples: a $CeO_2-ZrO_2$ support with 0% V, 1% $V/CeO_2-ZrO_2$, 3% $V/CeO_2-ZrO_2$, and 5% $V/CeO_2-ZrO_2$.

Specific surface area of the catalysts was measured using $N_2$ adsorption isotherms and Brunauer-Emmett-Teller (BET) analysis. Before the nitrogen adsorption, catalyst samples were degassed at 200° C. for 2 h under vacuum condition in order to remove adsorbates on the catalysts. The values of the measured surface areas are shown in Table 2.

TABLE 2

BET surface area of prepared catalysts.

| Sample | $CeO_2$—$ZrO_2$ support | 1% $V/$ $CeO_2$—$ZrO_2$ | 3% $V/$ $CeO_2$—$ZrO_2$ | 5% $V/$ $CeO_2$—$ZrO_2$ |
| --- | --- | --- | --- | --- |
| Surface area ($m^2/g$) | 163 | 105 | 111 | 108 |

Compositions of the catalysts were analyzed by X-ray Fluorescence (XRF, ZSX Primus II, Rigaku, Japan) and are shown in Table 3. The nominal values (wt %) of V content in the different catalyst samples are very close to the corresponding desired values set in the preparation procedure.

TABLE 3

Composition of the catalysts (wt%)

| | 1% V/CeO$_2$—ZrO$_2$ | 3% V/CeO$_2$—ZrO$_2$ | 5% V/CeO$_2$—ZrO$_2$ |
|---|---|---|---|
| ZrO$_2$ | 30.6 | 29.3 | 27.7 |
| CeO$_2$ | 68.0 | 66.9 | 66.5 |
| V | 1.4 | 3.8 | 5.8 |

EXAMPLE 3

Oxidative Dehydration of Methanol over 1% V/CeO$_2$-ZrO$_2$ Catalysts with Different O$_2$/CH$_3$OH Ratios The process of the oxidative dehydration of methanol was carried out using a microreactor (PID Eng & Tech, System, Spain) with a fixed bed quartz reactor at atmospheric pressure in the temperature range between 200 and 350° C. The reactor was charged with 0.1 g catalyst having a particle size between 0.08 to 0.1 mm. The catalyst bed was supported on a bed of quartz wool. The internal diameter of the quartz reactor was 4 mm, and the height of the catalyst bed was 7-8 mm. A K-type thermocouple was placed at the center of the catalyst bed to measure and control the reaction temperature.

Liquid methanol flow was controlled by a Bronkhorst High-Tech B.V. CEM system at 0.45 g·h$^{-1}$. Different oxygen (O$_2$) flows were employed and controlled by a mass flow controller (Bronkhorst High-Teck B.V.) to make gas streams having O$_2$/CH$_3$OH (mol/mol) ratios of 0.1, 0.2, 0.3, 0.4, or 0.5.

The required flows of methanol and oxygen were mixed with helium as a carrier gas in a mixing chamber heated at 150° C. The total flow of the gas mixture was 50 cm$^3$/min, at a gas hourly space velocity (GHSV), of 30,000 h$^{-1}$.

The catalyst bed was preheated to 150° C. prior to introducing the reactants. Upon introducing the gas mixture, the reactor temperature was increased to the desired reaction temperature in the range between 200-350° C. at a ramping rate of 5° C./min. For each reaction temperature, gas flow in the reactor was maintained for 3 h to reach steady state before analyzing the reaction products. The reactants and products were analyzed with an on-line connected gas chromatograph (HP, G1540A) equipped with TCD detectors. A molecular sieve 13X was used to separate O$_2$ and CO, and Porapak QS was used to separate H$_2$, CO$_2$, H$_2$O, CH$_2$O (formaldehyde), CH$_3$OH, and CH$_3$OCH$_3$ (dimethyl ether).

Conversion (%) of reactants and selectivity of products were calculated as follows.

$$CH_3OH\ conversion(\%) = \frac{mol\ of\ CH_3OH_{in} - mol\ of\ CH_3OH_{out}}{mol\ of\ CH_3OH_{in}} \times 100$$

$$O_2\ conversion(\%) = \frac{mol\ of\ O_{2_{in}} - mol\ of\ O_{2_{out}}}{mol\ of\ O_{2_{in}}} \times 100$$

$$CH_2O\ selectivity(\%) = \frac{mol\ of\ CH_2O}{mol\ of\ CH_3O_{consumed}} \times 100$$

$$CO\ selectivity(\%) = \frac{mol\ of\ CO}{mol\ of\ CH_3OH_{consumed}} \times 100$$

$$CO_2\ selectivity(\%) = \frac{mol\ of\ CO_2}{mol\ of\ CH_3OH_{consumed}} \times 100$$

$$DME(CH_3OCH_3)\ selectivity(\%) =$$
$$\frac{mol\ CH_3OH_{in} - (mol\ CH_3OH_{out} + mol\ CH_2O + mol\ CO + mol\ CO_2)}{mol\ CH_3OH_{consumed}} \times 100$$

$$DME\ yield(\%) = \frac{CH_3OH\ conversion(\%) \times DME\ selectivity(\%)}{100}$$

FIGS. 2, 3, 4, 5, 6, and 7 show CH$_3$OH conversion and product selectivity versus reaction temperature at O$_2$/CH$_3$OH ratios of 0, 0.1, 0.2, 0.3, 0.4, and 0.5, respectively, using 1% V/CeO$_2$-ZrO$_2$. The DME yield at each O$_2$/CH$_3$OH ratio used is shown in FIG. 8.

Figure 2:
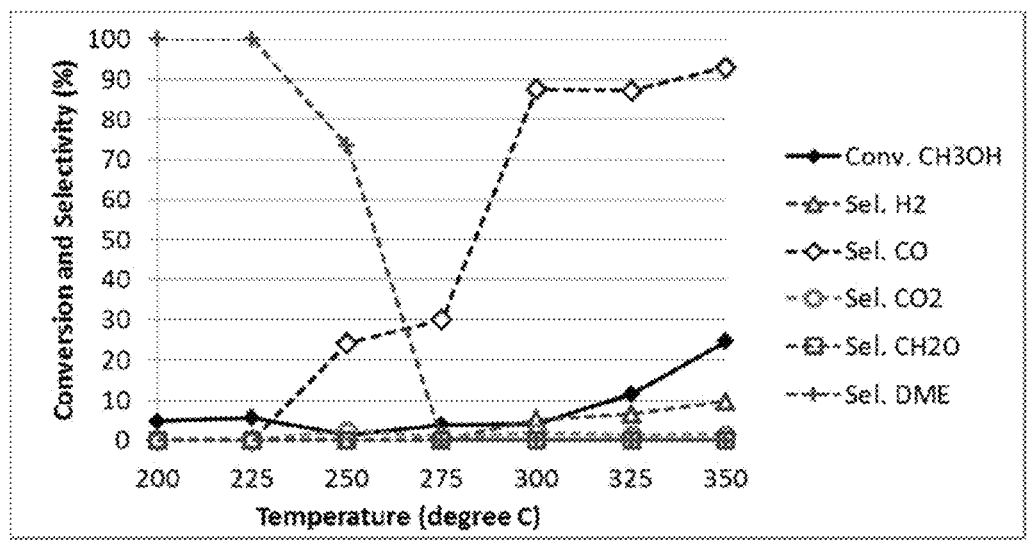
FIG. 2 shows reactant conversions and product selectivities obtained using a 1% V/$CeO_2$-$ZrO_2$ catalyst without $O_2$ over a temperature range of 200-350° C.
Figure 3:
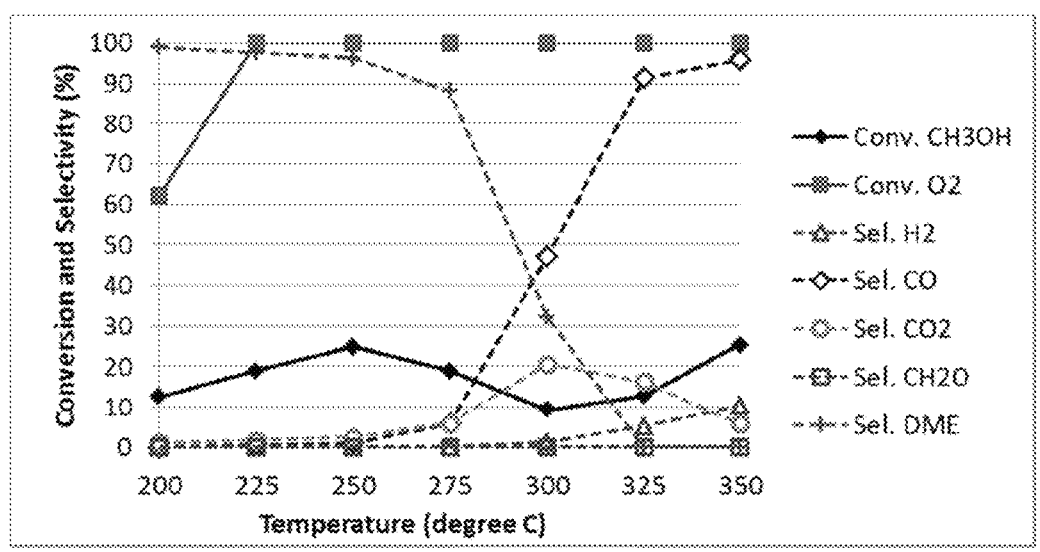
FIG. 3 shows reactant conversions and product selectivities obtained using a 1% V/$CeO_2$-$ZrO_2$ catalyst with an $O_2$/$CH_3OH$ molar ratio of 0.1 over a temperature range of 200-350° C.
Figure 4:
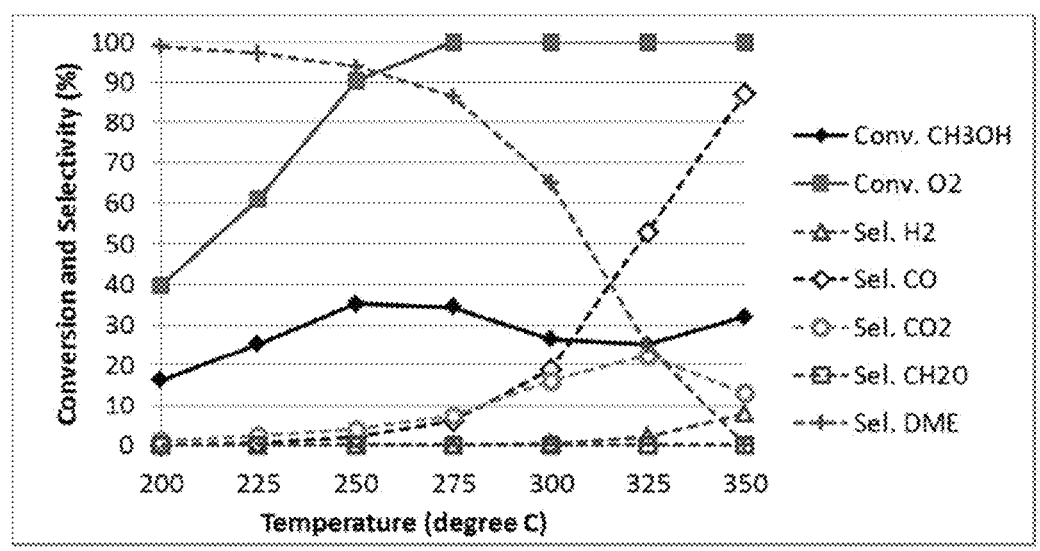
FIG. 4 shows reactant conversions and product selectivities obtained using a 1% V/$CeO_2$-$ZrO_2$ catalyst with an $O_2$/$CH_3OH$ molar ratio of 0.2 over a temperature range of 200-350° C.
Figure 5:
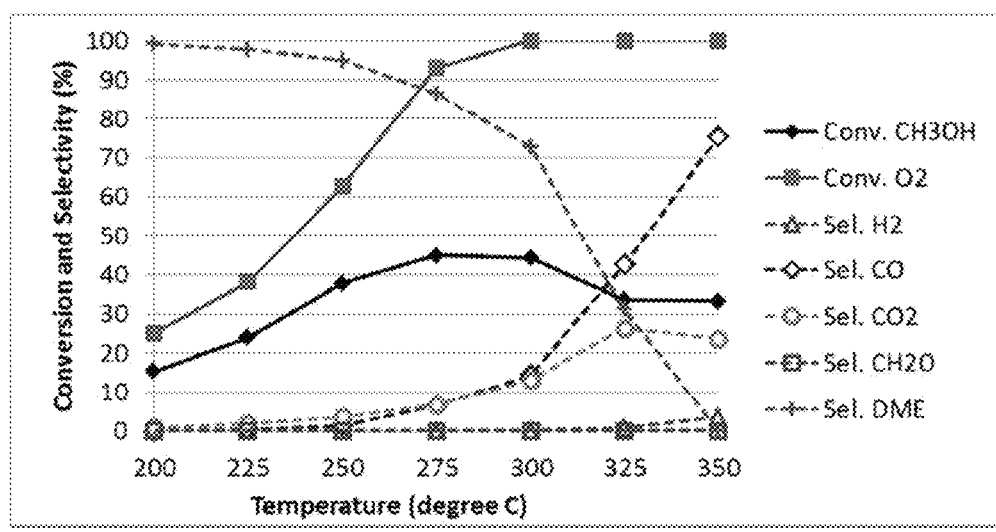
FIG. 5 shows reactant conversions and product selectivities obtained using a 1% V/$CeO_2$-$ZrO_2$ catalyst with an $O_2$/$CH_3OH$ molar ratio of 0.3 over a temperature range of 200-350° C.
Figure 6:
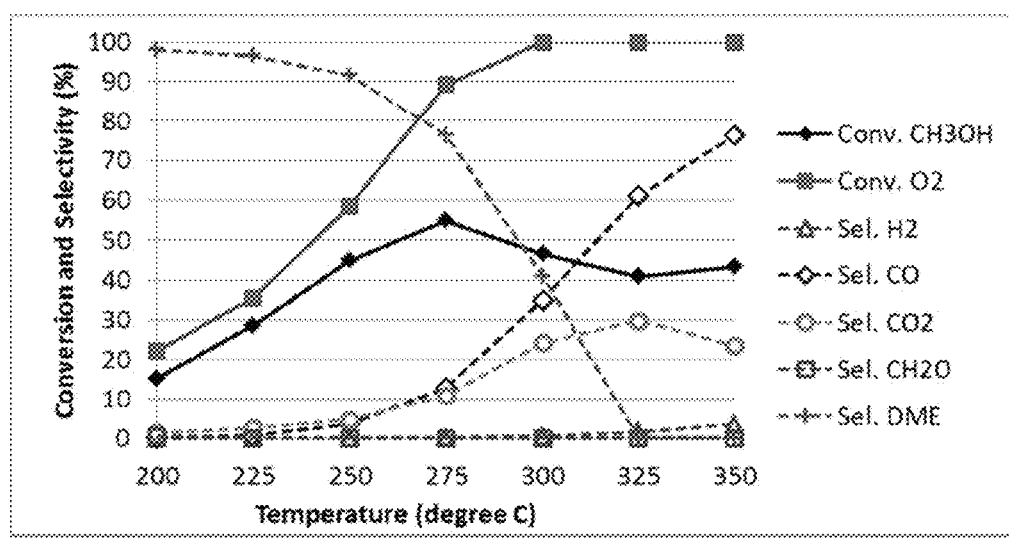
FIG. 6 shows reactant conversions and product selectivities obtained using a 1% V/$CeO_2$-$ZrO_2$ catalyst with an $O_2$/$CH_3OH$ molar ratio of 0.4 over a temperature range of 200-350° C.
Figure 7:
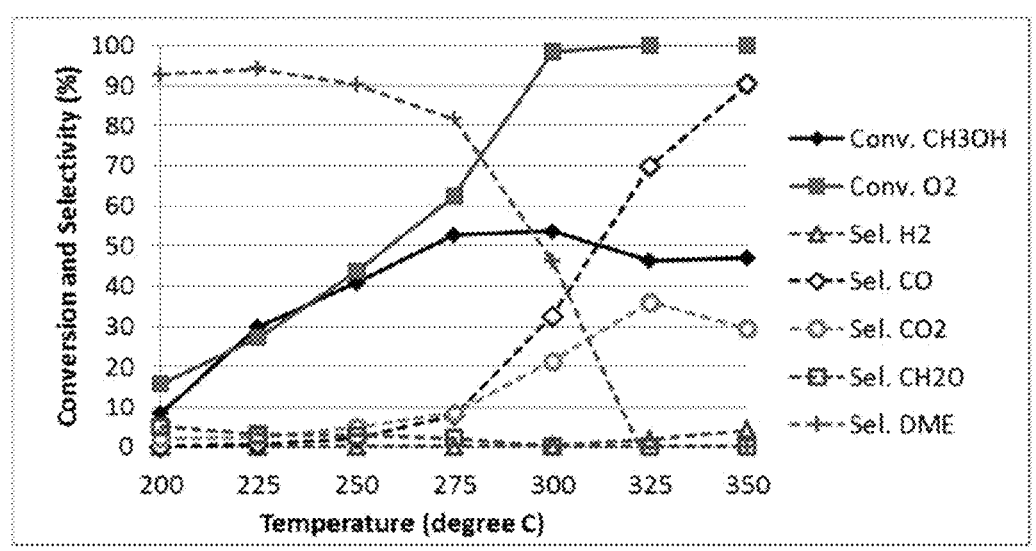
FIG. 7 shows reactant conversions and product selectivities obtained using a 1% V/$CeO_2$-$ZrO_2$ catalyst with an $O_2$/$CH_3OH$ molar ratio of 0.5 over a temperature range of 200-350° C.

FIGS. 2 and 8 reveal that little to no conversion of CH$_3$OH was observed in the reaction temperature range between 200 and 250° C. when no oxygen was added to the reaction mixture (O$_2$/CH$_3$OH ratio of 0). The minute conversion of methanol in this temperature range depicted in FIG. 2 is attributed to flow controller errors.

When O$_2$ was added to the reaction mixture at various O$_2$/CH$_3$OH ratios of 0.1, 0.2, 0.3, 0.4, and 0.5, a considerable amount of methanol was converted and DME was obtained as a main product in the temperature range between 200 and 350° C. DME yield was significantly increased with an increase in the O$_2$/CH$_3$OH ratio in the range between 0.1 to 0.5, as shown in FIG. 8. These results illustrate that DME production using a V/CeO$_2$-ZrO$_2$ catalyst requires oxygen and follows a different mechanism compared to the dehydration mechanism of methanol on γ-Al$_2$O$_3$ or zeolite catalysts.

A reaction temperature at 250° C. provides both a high methanol conversion and a high DME selectivity. Moreover, the dependence of methanol conversion and selectivity to DME, CO, and CO$_2$ at 250° C. on O$_2$/CH$_3$OH ratio is shown in FIG. 9. This figure shows that an O$_2$/CH$_3$OH ratio of 0.3 provides an ideal combination of methanol conversion and DME selectivity. Higher O$_2$/CH$_3$OH molar ratios lead to higher selectivities of CO and CO$_2$, and a relatively lower DME selectivity. Thus, it is concluded that the best reaction conditions for the oxidative dehydration of methanol to DME for the highest methanol conversion and selectivity to DME are a reaction temperature at 250° C. and a 0.3 O$_2$/CH$_3$OH molar ratio.

EXAMPLE 4

Figure 10:
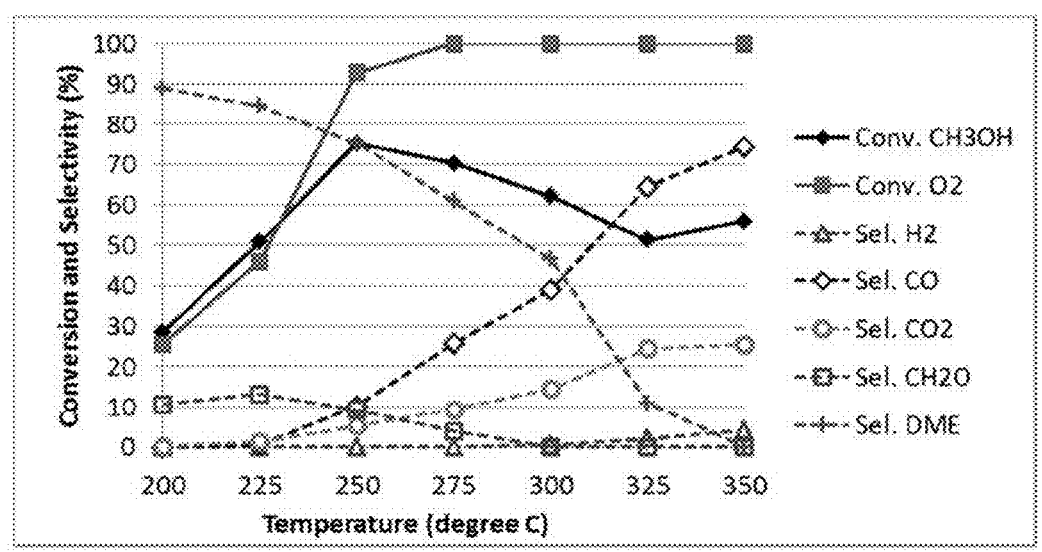
FIG. 10 shows reactant conversions and product selectivities obtained using a 3% V/$CeO_2$-$ZrO_2$ catalyst with an $O_2$/$CH_3OH$ molar ratio of 0.5 over a temperature range of 200-350° C.
Figure 11:
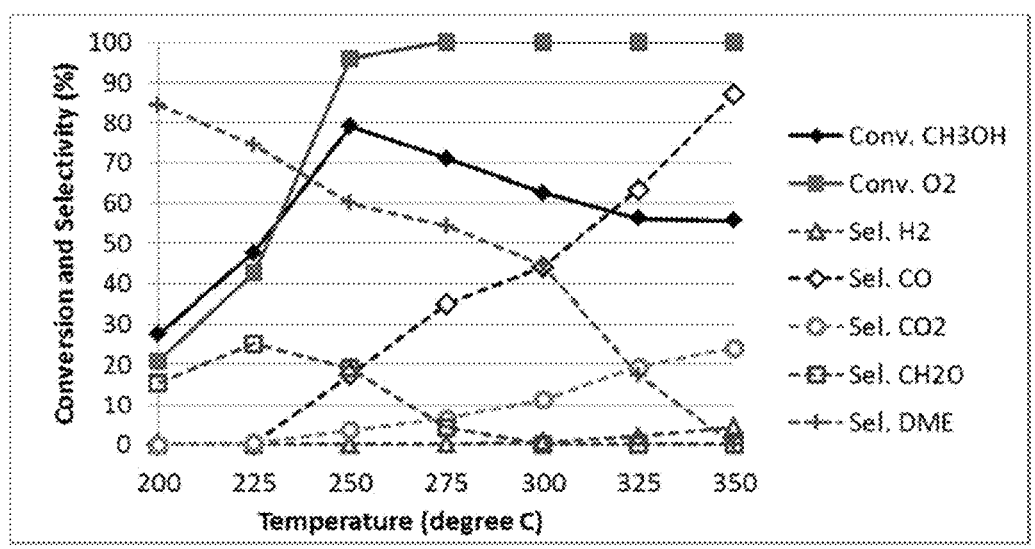
FIG. 11 shows reaction conversions and product selectivities obtained using a 5% V/$CeO_2$-$ZrO_2$ catalyst with an $O_2$/$CH_3OH$ molar ratio of 0.5 over a temperature range of 200-350° C.

Oxidative Dehydration of Methanol Over V/CeO$_2$-ZrO$_2$ Catalysts at Different wt % of V Content Activity of 3% V/CeO$_2$-ZrO$_2$ and 5% V/CeO$_2$-ZrO$_2$ catalyst samples were tested with an O$_2$/CH$_3$OH molar ratio of 0.5 and with a similar procedure as that followed in Example 3. These results for 3% V/CeO$_2$-ZrO$_2$ and 5% V/CeO$_2$-ZrO$_2$ catalyst samples are shown in FIGS. 10 and 11, respectively. A comparison of DME Yield achieved using different V content in V/CeO$_2$-ZrO$_2$ catalysts is shown in FIG. 12. These data show that although an increase of V content provides an increase in methanol conversion at the ideal reaction temperature of 250° C., however, it also leads to a decrease in DME selectivity and an increase in selectivity of formaldehyde (CH$_2$O) and carbon monoxide (CO) as shown in FIG. 13. The data also reveal that the 3% vanadium sample produces both high methanol conversion and high DME selectivity, which lead to that sample being the best for producing DME with a high DME yield.

EXAMPLE 5

Stability Test of V/CeO$_2$-ZrO$_2$ Catalysts

Methanol oxidative dehydration reaction over 1% V/CeO$_2$-ZrO$_2$ was isothermally performed at 250° C. and an O$_2$/CH$_3$OH molar ratio of 0.3 in order to examine the stability of the catalysts. Test results reveal that 1% V/CeO$_2$-ZrO$_2$ does not show any significant deactivation or decrease in DME selectivity over a reaction time period of 70 hours, as shown in FIG. 14. Methanol conversion and DME selectivity are maintained at stable values throughout the reaction period at about 38% and 92%, respectively.

Overall, the invention of the above examples uses a novel concept of reaction and catalyst to produce DME from methanol by adding oxygen to the reaction mixture over the developed catalyst. Vanadium oxide was supported on a mixture of cerium oxide (CeO$_2$) and zirconium oxide (ZrO$_2$) with a gravimetric ratio of CeO$_2$:ZrO$_2$=3:1, by an incipient wetness impregnation method.

V/CeO$_2$-ZrO$_2$ catalyst produces DME by oxidative dehydration of methanol with high selectivity, and oxygen is necessary in the reactant stream to produce DME.

The catalyst showed a high catalytic stability. The 1% V/CeO$_2$-ZrO$_2$ sample did not show any significant deactivation or decrease in DME selectivity during a reaction run of 70 h at 250° C. The highest DME yield was obtained at the reaction temperature of 250° C. and O$_2$/CH$_3$OH feed ratio of 0.5 over a 3% V/CeO$_2$-ZrO$_2$ catalyst, as shown in FIG. 12.

The invention claimed is:

1. A CeO$_2$ and ZrO$_2$ supported vanadium oxide catalyst, comprising:
    0.1-10 wt % vanadium;
    65-80 wt % CeO$_2$; and
    20-32 wt % ZrO$_2$,
    wherein the catalyst is in the form of microparticles with diameters of 50-200 μm.

2. The CeO$_2$ and ZrO$_2$ supported vanadium oxide catalyst of claim 1, which has a surface area of 80-150 m$^2$/g.

3. The CeO$_2$ and ZrO$_2$ supported vanadium oxide catalyst of claim 1, which has a Ce to Zr molar ratio of 1.4:1-3.5:1.

4. The CeO$_2$ and ZrO$_2$ supported vanadium oxide catalyst of claim 1, wherein the vanadium oxide is V$_2$O$_5$.

5. A method for producing the CeO$_2$ and ZrO$_2$ supported vanadium oxide catalyst of claim 1, comprising:
    mixing a CeO$_2$ powder, a ZrO$_2$ powder, a vanadium compound, and water to form a solution;
    drying the solution to produce a dried catalyst precursor;
    heating the dried catalyst precursor at 450-700° C. for 2-8 hours to produce a calcined powder;
    pelletizing and grinding the calcined powder to produce the CeO$_2$ and ZrO$_2$ supported vanadium oxide catalyst.

6. The method of claim 5, wherein the solution has a vanadium concentration of 0.05-1.0 M.

7. The method of claim 5, wherein the vanadium compound is one selected from the group consisting of ammonium metavanadate, potassium metavanadate, sodium metavanadate, bismuth vanadate, vanadium oxytrichloride, vanadium pentafluoride, and vanadium oxide.

8. The method of claim 7, wherein the vanadium compound is ammonium metavanadate.

9. A method of dehydrating methanol into dimethyl ether comprising:
    feeding a gas stream comprising O$_2$ and methanol to a fixed bed flow reactor comprising the CeO$_2$ and ZrO$_2$ supported vanadium oxide catalyst of claim 1 at a temperature of 200-300° C. to produce dimethyl ether and at least one side product selected from the group consisting of hydrogen gas, carbon monoxide, carbon dioxide, water, and formaldehyde.

10. The method of claim 9, wherein the gas stream has an O$_2$ to methanol molar ratio of 0.2:1-0.6:1.

11. The method of claim 9, wherein the gas stream is fed to the fixed bed flow reactor at a gas hourly space velocity of 25,000-35,000 h$^{-1}$.

12. The method of claim 9, wherein a selectivity percentage for dimethyl ether from the conversion of methanol is at least 90%.

13. The method of claim 9, wherein a percentage yield of dimethyl ether, relative to a mol % of methanol that is converted, is at least 30%.

* * * * *